(12) United States Patent
Blaber et al.

(10) Patent No.: US 9,783,587 B1
(45) Date of Patent: Oct. 10, 2017

(54) SYNTHETIC FOLDABLE PROTEINS GENERATED FROM PEPTIDE SEGMENTS OF FOLDING NUCLEI OF REFERENCE PROTEINS

(71) Applicant: Florida State University Research Foundation, Inc., Tallahassee, FL (US)

(72) Inventors: Michael Blaber, Tallahassee, FL (US); Liam M. Longo, Port St. Lucie, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 40 days.

(21) Appl. No.: 14/707,691

(22) Filed: May 8, 2015

Related U.S. Application Data

(60) Provisional application No. 61/990,838, filed on May 9, 2014.

(51) Int. Cl.
  C07K 14/50 (2006.01)
  G06F 19/28 (2011.01)
  G06F 19/16 (2011.01)
  G01N 23/20 (2006.01)

(52) U.S. Cl.
  CPC ............ *C07K 14/50* (2013.01); *G01N 23/20* (2013.01)

(58) Field of Classification Search
  None
  See application file for complete search history.

(56) References Cited

U.S. PATENT DOCUMENTS

| | | |
|---|---|---|
| 5,219,569 A | 6/1993 | Blaber et al. |
| 7,595,296 B1 | 9/2009 | Blaber et al. |
| 7,659,379 B1 | 2/2010 | Blaber et al. |
| 7,696,171 B1 | 4/2010 | Blaber et al. |
| 7,754,216 B2 | 7/2010 | Scarisbrick et al. |
| 7,776,825 B1 | 8/2010 | Blaber et al. |
| 7,790,682 B1 | 9/2010 | Blaber et al. |
| 8,119,776 B1 | 2/2012 | Blaber et al. |
| 8,153,770 B1 | 4/2012 | Blaber et al. |
| 8,153,771 B1 | 4/2012 | Blaber et al. |
| 8,461,111 B2 | 6/2013 | Blaber et al. |
| 8,962,557 B2 | 2/2015 | Blaber et al. |
| 2002/0146731 A1 | 10/2002 | Sanli et al. |
| 2006/0127391 A1 | 6/2006 | Scarisbrick et al. |
| 2010/0298220 A1 | 11/2010 | Blaber et al. |
| 2011/0008789 A1 | 1/2011 | Scarisbrick et al. |
| 2011/0224404 A1 | 9/2011 | Blaber et al. |
| 2013/0130983 A1 | 5/2013 | Blaber et al. |
| 2013/0323262 A1 | 12/2013 | Scarisbrick et al. |
| 2014/0045751 A1 | 2/2014 | Blaber |
| 2015/0148293 A1 | 5/2015 | Blaber et al. |
| 2015/0361149 A1 | 12/2015 | Blaber et al. |

FOREIGN PATENT DOCUMENTS

| | | |
|---|---|---|
| WO | 2010135491 A2 | 11/2010 |
| WO | 2014024173 A9 | 4/2014 |
| WO | 2015198175 A1 | 12/2015 |
| WO | 2016089945 A1 | 6/2016 |

OTHER PUBLICATIONS

Longo et al., 2012, Protein Science vol. 21, p. 1911-1920.*
Lee et al. PNAS, vol. 108, No. 1, p. 126-130.*
Ferscht et al. PNAS, 2004 101, 21, 7976-7981.*
Blaber et al. Biophysical Journal, 77, 1999, 470-477.*
Galzitskaya, Oxana V., Ivankov, Dmitry N., Finkelstein, Alexei, V.,:"Folding Nuclei in Proteins"; Institute of Protein Research, Russian Academy of Sciences; Jan. 15, 2001.
Lee, Jihun; Blaber, Michael; "Experimental Support for the Evolution of Symmetric Protein Architecture from a Simple Peptide Motif"; 126-130; PNAS; Jan. 4, 2011; vol. 108, No. 1.
Longo, Liam M., Kumru, Ozan S., Middaugh, C. Russell, Blaber, Michael; "Evolution and Design of Protein Structure by Folding Nucleus Symmetric Expansion"; Structure 22, 1-8; Oct. 7, 2014.
Mirny, Leonid; Shakhnovich, Eugene; "Evolutionary Conservation of the Folding Nucleus"; J. Mol. Biol.; 2001; pp. 123-129.

* cited by examiner

*Primary Examiner* — Michael Borin
(74) *Attorney, Agent, or Firm* — Christopher M. Ramsey; GrayRobinson, P.A.

(57) ABSTRACT

A method of making a synthetic foldable having a tertiary structure emulating the tertiary structure of a reference foldable protein is described. The method includes determining a folding nucleus peptide sequence associated with folding the reference foldable protein. The synthetic foldable protein is synthesized by including the determined folding nucleus peptide sequence and at least one repeat thereof in the peptide sequence of the synthetic foldable protein.

14 Claims, 8 Drawing Sheets
(3 of 8 Drawing Sheet(s) Filed in Color)

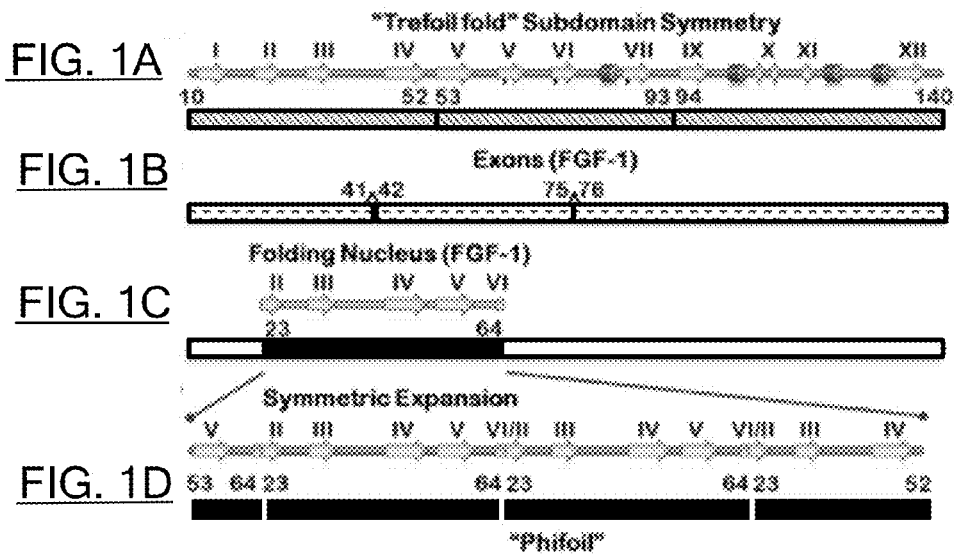

FIG. 1A
FIG. 1B
FIG. 1C
FIG. 1D

```
            15           20           25           30           35           40           45           50  52
Phifoil  E V Y I K S T E T G Q Y L R I L P D G T V D G T R D R S D Q H I Q L Q L S A E S V G
FGF-1    P K L L Y C S N G G H F L R I L P D G T V D G T R D R S D Q H I Q L Q L S A E S V G
            55           60           65           70           75           80           85           90  93
Phifoil  E V Y I K S T E T G Q Y R I L P D G T V D G T R D R S D Q H I Q L Q L S A E S V G
FGF-1    E V Y I K S T E T G Q Y A M D T D G L L Y G S - Q T P N E E C L F L E R L E E N H
            95          100          105          110          115      123A 125          130          135  140
Phifoil  E V Y I K S T E T G Q Y L R I L P D G T V D G T R D R S D Q H I Q L Q L S A E S V G
FGF-1    Y N T Y I S K K H A W F V G L K K N G S C K R T - H Y G Q K A I L F L P L P V S S D
                              E   N                       120 G   R
                           105 K                              P
```

FGF-1 = SEQ ID NO: 1
Phifoil = SEQ ID NO: 2

FIG. 2

| | Phifoil[a] |
|---|---|
| Space group | P212121 |
| Cell constants (Å) | a = 52.9 |
| | b = 68.6 |
| | c = 76.0 |
| | α = 90° |
| | β = 90° |
| | γ = 90° |
| Max Resolution (Å) | 2.15 |
| Mosaicity (°) | 0.48 |
| Redundancy | 2.2 |
| Mol/ASU | 2 |
| Matthews coeff. (Å$^3$/Da) | 2.50 |
| Total reflections | 27,752 |
| Unique reflections | 12,829 |
| I/σ (overall) | 18.8 |
| I/σ (highest shell[b]) | 4.1 |
| Completion overall (%) | 81.7 |
| Completion highest shell[b] (%) | 86.9 |
| $R_{merge}$ overall (%) | 8.0 |
| Rmerge highest shellb (%) | 19.6 |
| Nonhydrogen protein atoms | 1,939 |
| Solvent molecules/ion | 132/1 |
| $R_{cryst}$ (%) | 22.8 |
| $R_{free}$ (%) | 26.7 |
| Rmsd bond length (Å) | 0.005 |
| Rmsd bond angle (°) | 0.94 |
| Ramachandran plot | |
| Most favored (%) | 97.5 |
| Additional allowed (%) | 2.5 |
| Generously allowed (%) | 0 |
| Disallowed region (%) | 0 |
| PDB accession | 4OW4 |

[a] 800 mM $(NH_4)_2SO_4$, 100 mM citric acid, pH 4.0.
[b] Highest shell 2.21–2.15 Å

FIG. 4

Core packing comparison of Phifoil and FGF-1

| Position | FGF-1 (2AFG) | Side chain Access (Å²)[a] | Side chain vol (Å³)[b] | Phifoil | Side chain Access (Å²) | Side chain vol (Å³)[b] |
|---|---|---|---|---|---|---|
| 14 | Leu | 2.7 | 167.4 | Ile | 0.0 | 167.9 |
| 23 | Leu | 0.3 | 167.4 | Leu | 0.0 | 167.4 |
| 25 | Ile | 0.0 | 167.9 | Ile | 0.0 | 167.9 |
| 31 | Val | 0.0 | 125.1 | Val | 0.0 | 125.1 |
| 44 | Leu | 0.0 | 167.4 | Leu | 0.0 | 167.4 |
| 56 | Ile | 1.0 | 167.9 | Ile | 0.0 | 167.9 |
| 65 | Leu | 0.4 | 167.4 | Leu | 0.0 | 167.4 |
| 67 | Met | 0.7 | 172.6 | Ile | 0.0 | 167.9 |
| 73 | Leu | 0.4 | 167.4 | Val | 0.0 | 125.1 |
| 85 | Phe | 0.0 | 215.4 | Leu | 0.0 | 167.4 |
| 97 | Tyr | 0.1 | 221.4 | Ile | 0.0 | 167.9 |
| 109 | Val | 2.6 | 125.1 | Leu | 0.0 | 167.4 |
| 111 | Leu | 0.0 | 167.4 | Ile | 0.0 | 167.9 |
| 117 | Cys | 7.4 | 82.1 | Val | 0.0 | 125.1 |
| 132 | Phe | 0.3 | 215.4 | Leu | 0.0 | 167.4 |
| Total: | | 15.9 | 2,497.3 | | 0.0 | 2,387.1 |

[a] Calculated using EDPDB software
[b] Calculated from partial molar volumes

FIG. 5

Isothermal equilibrium denaturation of FGF-1 and Phifoil.

| Protein | $\Delta G_{unf}$ (kJ/mol) | m-value (kJ/mol/M) | $C_m$ (M) |
|---|---|---|---|
| FGF-1[a] | 21.1 ± 0.6 | 18.9 ± 0.6 | 1.11 ± 0.01 |
| Phifoil | 20.7 ± 0.3 | 17.5 ± 0.3 | 1.18 ± 0.01 |

[a] Reported in Brych, et al., *J. Mol. Biol.*, 344, 769-780 (2004).

FIG. 6

| DSC data for the thermal denaturation of FGF-1 and Phifoil (ADA buffer). | | | |
|---|---|---|---|
| Protein | $\Delta H(T_m)$ (kJ mol$^{-1}$) | $T_m$ (°C) | $\Delta H_{vH}/\Delta H_{cal}$ |
| 0 M GuHCl | | | |
| FGF-1[a] | ppt[b] | ppt | ppt |
| Phifoil | 269 ± 2 | 56.0 ± 0.1 | 1.00 ± 0.03 |
| 0.7 M GuHCl | | | |
| FGF-1[a] | 257 ± 3 | 39.4 ± 0.1 | 1.08 |
| Phifoil | 217 ± 11 | 47.9 ± 0.7 | 1.00 ± 0.15 |

[a]Reported in Blaber, et al., *Biophys. J.*, 77, 470-477 (2004).
[b]Precipitation

FIG. 7

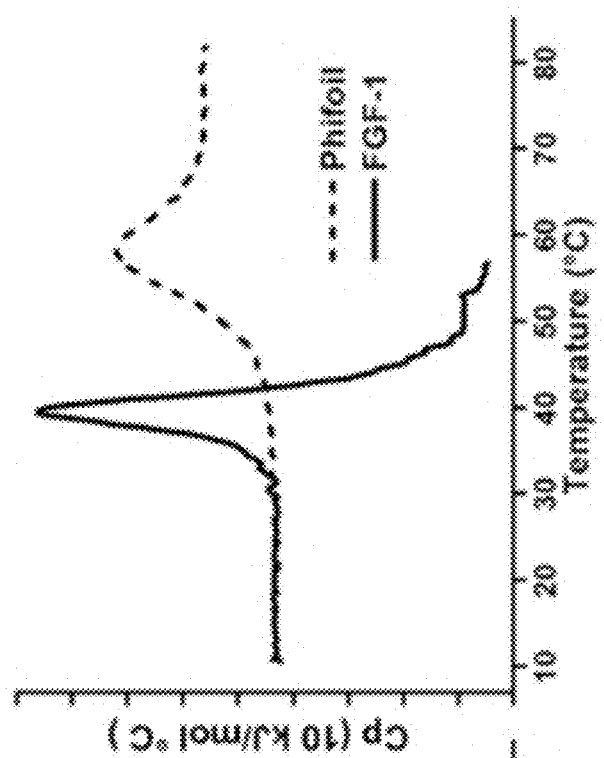
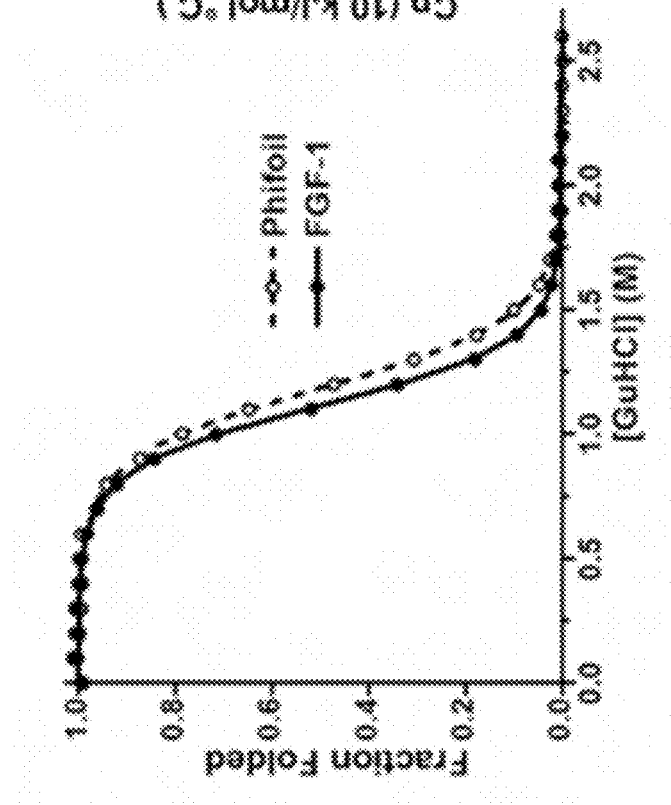
FIG. 9A
FIG. 9B

SEQUENCE LISTING

<160> NUMBER OF SEQ ID NOS: 3

<210> SEQ ID NO 1
<211> LENGTH: 128
<212> TYPE: PRT
<213> ORGANISM: Homo sapiens -continued

<400> SEQUENCE: 1

Pro Lys Leu Leu Tyr Cys Ser Asn Gly Gly His Phe Leu Arg Ile Leu
1               5                   10                  15

Pro Asp Gly Thr Val Asp Gly Thr Arg Asp Arg Ser Asp Gln His Ile
            20                  25                  30

Gln Leu Gln Leu Ser Ala Glu Ser Val Gly Glu Val Tyr Ile Lys Ser
        35                  40                  45

Thr Glu Thr Gly Gln Tyr Leu Ala Met Asp Thr Asp Gly Leu Leu Tyr
    50                  55                  60

Gly Ser Gln Thr Pro Asn Glu Glu Cys Leu Phe Leu Glu Arg Leu Glu
65                  70                  75                  80

Glu Asn His Tyr Asn Thr Tyr Ile Ser Lys Lys His Ala Trp Phe Val
                85                  90                  95

Gly Leu Lys Lys Asn Gly Ser Cys Cys Lys Arg Gly Pro Arg Thr His
            100                 105                 110

Tyr Gly Gln Lys Ala Ile Leu Phe Leu Pro Leu Pro Val Ser Ser Asp
        115                 120                 125

<210> SEQ ID NO 2
<211> LENGTH: 126
<212> TYPE: PRT
<213> ORGANISM: Artificial Sequence
<220> FEATURE:
<223> OTHER INFORMATION: SYNTHETIC PEPTIDE

<400> SEQUENCE: 2

Glu Val Tyr Ile Lys Ser Thr Glu Thr Gly Gln Tyr Leu Arg Ile Leu
1               5                   10                  15

Pro Asp Gly Thr Val Asp Gly Thr Arg Asp Arg Ser Asp Gln His Ile
            20                  25                  30

Gln Leu Gln Leu Ser Ala Glu Ser Val Gly Glu Val Tyr Ile Lys Ser
        35                  40                  45

Thr Glu Thr Gly Gln Tyr Leu Arg Ile Leu Pro Asp Gly Thr Val Asp
    50                  55                  60

Gly Thr Arg Asp Arg Ser Asp Gln His Ile Gln Leu Gln Leu Ser Ala
65                  70                  75                  80

Glu Ser Val Gly Glu Val Tyr Ile Lys Ser Thr Glu Thr Gly Gln Tyr
                85                  90                  95

Leu Arg Ile Leu Pro Asp Gly Thr Val Asp Gly Thr Arg Asp Arg Ser
            100                 105                 110

Asp Gln His Ile Gln Leu Gln Leu Ser Ala Glu Ser Val Gly
        115                 120                 125

<210> SEQ ID NO 3
<211> LENGTH: 43
<212> TYPE: PRT
<213> ORGANISM: Artificial Sequence
<220> FEATURE:
<223> OTHER INFORMATION: Synthetic polypeptide

```
<400> SEQUENCE: 3

Leu Arg Ile Leu Pro Asp Gly Thr Val Asp Gly Thr Arg Asp Arg Ser
1               5                   10                  15

Asp Gln His Ile Gln Leu Gln Leu Ser Ala Glu Ser Val Gly Glu Val
                20                  25                  30

Tyr Ile Lys Ser Thr Glu Thr Gly Gln Tyr Leu
            35                  40
```

SYNTHETIC FOLDABLE PROTEINS GENERATED FROM PEPTIDE SEGMENTS OF FOLDING NUCLEI OF REFERENCE PROTEINS

CROSS-REFERENCE TO RELATED APPLICATION

This claims the benefit of U.S. provisional application Ser. No. 61/990,838, filed May 9, 2014, which is incorporated by reference in its entirety.

FIELD OF THE INVENTION

This relates to the field of proteins and, more particularly, to protein synthesis and design.

SEQUENCE LISTING

The application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated by reference herein in its entirety.

BACKGROUND

Proteins are biomolecules made of amino acids linked together by peptide bonds to form amino acid sequences. Proteins perform a plethora of important functions in nature. Those functions are governed by their amino acid sequences and structure.

Proteins fold into complicated three-dimensional structures, which are characterized by four different structural terms. The primary structure of a protein is the linear representation of the protein's amino acid sequence. The secondary structure is the three-dimensional form of local segments of the protein, such as alpha-helices and beta-sheets. The tertiary structure is the protein's overall three-dimensional shape, fold, or architecture. The quaternary structure is the assembly of multiple polypeptide chains into a larger protein assembly, sometimes referred to as oligomeric assembly.

The tertiary structure forms through a process called "protein folding" in which some of the protein's amino acids interact with each other to cause the protein to fold into its three-dimensional conformation. Although the structure of a folded protein is complex, it is often symmetric to some degree. Therefore, in a symmetric protein, the tertiary structure can be simplified as a series of structural regions that appear multiple times in the protein.

Amino acid sequence segments that play a key role in folding a protein form what is called a "folding nucleus." Studies have shown that the folding nucleus typically includes one-third to one-half of the overall polypeptide chain of single-domain globular proteins. Folding nuclei may be difficult to identify as they are not always defined by exon boundaries or contained neatly within an apparent structural repeating motif; they are considered to be a "cryptic" region within a protein. It appears that the presence of a folding nucleus is a protein design requirement, but there is no clear recipe for using a folding nucleus in protein design or how to complete the design of the remaining segments of the polypeptide to produce a robustly foldable protein.

BRIEF SUMMARY

This problem is overcome by designing proteins using folding peptide segments from a folding nucleus of a reference protein to form folding nuclei in synthetic proteins. The folding peptide segments are repeated throughout the synthetic protein's primary structure to form the remainder of the polypeptide sequence. This technique advantageously produces stable folding proteins.

A method of making a foldable protein embodying this design principle includes determining a folding nucleus peptide sequence associated with folding a reference foldable protein. The reference foldable protein has a tertiary structure. A synthetic foldable protein having a tertiary structure emulating the tertiary structure of the reference foldable protein is synthesized by including the determined folding nucleus peptide sequence and at least one repeat thereof in the peptide sequence of the synthetic foldable protein.

The step of determining the folding nucleus peptide sequence of the reference foldable protein may include identifying the folding nucleus of the reference foldable protein by performing "$\phi$-value" analysis on the reference foldable protein.

The number of symmetry operations that can be performed on the reference foldable protein may be equal to a number of tandem repeats of the determined folding nucleus peptide sequence in the peptide sequence of the synthetic foldable protein.

In a particular embodiment, the synthetic foldable protein includes SEQ ID NO: 2.

In a particular embodiment, the reference foldable protein is native human FGF-1.

In a particular embodiment, the folding nucleus peptide sequence includes SEQ ID NO: 3.

Examples of tertiary structure that may be emulated include $\beta$-trefoil, TIM-barrel, or beta-propeller structures.

The tertiary structure of the synthetic foldable protein may have substantially the same symmetry as the tertiary structure of the reference foldable protein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a diagram showing a secondary structure schematic of FGF-1 with the repeating "trefoil-fold" structural subdomains indicated by different colors and associated secondary structure elements. Arrows=$\beta$-strands, cylinders=helices, and grey bars=loops/surface turns. The amino acid numbering scheme of the 140 amino acid form of FGF-1 is used throughout.

FIG. 1B is a diagram showing the intron-exon structure of the FGF-1 gene.

FIG. 1C is a diagram showing the location of the folding nucleus of FGF-1 as determined from experimental $\phi$-value analysis.

FIG. 1D is a diagram showing the Phifoil design based on the folding nucleus of FGF-1 expanded by the threefold symmetry of the $\beta$-trefoil target architecture and the associated secondary structure elements derived from FGF-1.

FIG. 2 shows that the primary structures of FGF-1 and Phifoil are arranged according to the three repeating trefoil-fold subdomains in FIG. 1A. The numbering scheme is based upon FGF-1 (relative gaps or insertions are indicated). The dark shading of contiguous amino acid positions 23-64 identify the folding nucleus of FGF-1 that was expanded by the threefold symmetry of the β-trefoil architecture to construct the Phifoil protein. The lighter shaded positions identify identical amino acids between FGF-1 and Phifoil in the remaining regions of the protein.

FIG. 4 is a table of the X-ray crystallography data collection refinement and refinement statistics for Phifoil.

FIG. 5 is a table of the X-ray crystallography core-packing parameters of Phifoil and FGF-1.

FIG. 6 is a table showing results from isothermal equilibrium and denaturation experiments on FGF-1 and Phifoil.

FIG. 7 is a table showing results from differential scanning calorimetry experiments on FGF-1 and Phifoil.

FIG. 9A is a line graph showing isothermal equilibrium denaturation of Phifoil and FGF-1 by GuHCl. The solid lines are the two-state model fit to the data points.

FIG. 9B is a line graph of differential scanning calorimetry endotherms of FGF-1 (solid line) and Phifoil (dashed line).

DETAILED DESCRIPTION OF PREFERRED EMBODIMENTS

Figure 3:
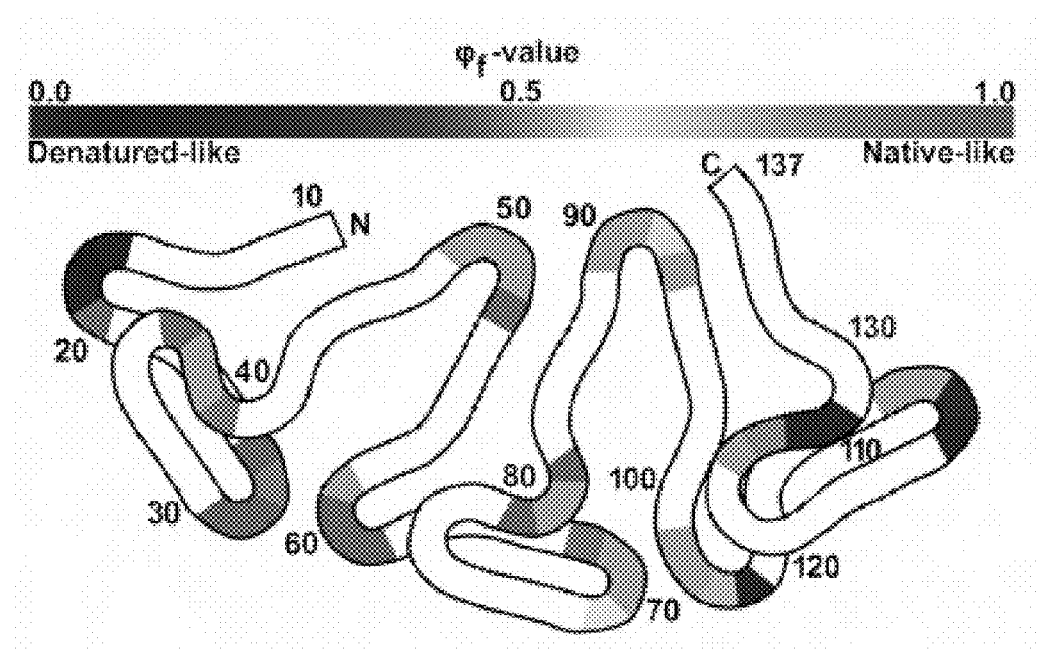
FIG. 3 is a color-coded two-dimensional diagram of Phifoil, indicating regions with different experimental ϕ-values.

An exemplary method of making a synthetic foldable protein is first described. The synthetic foldable protein is made using a peptide sequence from a folding nucleus of a reference protein. By repeating the peptide sequence from the folding nucleus, the resulting synthetic protein folds in such a way that it emulates the tertiary structure of the reference foldable protein even though the primary structure of the synthetic foldable protein and reference protein may be different. The method is advantageous because it provides a technique to synthesize new proteins with a desired architecture by symmetrically expanding the peptide sequence of the folding nucleus of the reference protein.

In more detail, the method of making a foldable protein includes (a) determining the folding nucleus peptide sequence associated with folding the reference foldable protein and (b) synthesizing the synthetic foldable protein by including the determined folding nucleus peptide sequence and at least one repeat thereof in the peptide sequence of the synthetic foldable protein. The synthetic foldable protein will have a tertiary structure emulating the tertiary structure of the reference foldable protein.

The reference foldable protein is a protein having a tertiary structure that one desires the synthetic protein to emulate. The reference protein may be selected from many different proteins and is not limited to proteins with only a particular tertiary structure or symmetry. A particular example of such a reference protein is human fibroblast growth factor 1 ("FGF-1"), which has a β-trefoil structure—a single-domain globular protein architecture having threefold internal rotational symmetry. FGF-1 is used in the Example to illustrate the method. Other exemplary tertiary structures that may be emulated using the method include, but are not limited to, TIM-barrel or beta-propeller structures.

The peptide sequence of the folding nucleus of the reference protein can be determined by various computational and/or experimental techniques. Through a computational technique, the reference protein can be modeled on a computer and the folding nucleus determined by having the computer identify the peptide sequence(s) that play a role in folding the protein.

A suitable experimental technique for identifying the folding nucleus of the reference protein is called ϕ-value analysis. In ϕ-value analysis, the degree of participation of a particular residue in a folding nucleus is determined by that residue's ϕ-value. ϕ is defined as $\Delta \ln k_f / \ln K$ where $k_f$ is the rate constant for folding and K is the equilibrium constant ($k_{folded}/k_{unfolded}$). ϕ=1 means that the residue has its native conformation in the folding transition state and is in the folding nucleus. ϕ=0 means that the residue is in the unfolded state in the folding transition state. The values of ϕ between 0 and 1 mean that the residue may be in the folding nucleus or is another folding nucleus associated with a different folding pathway.

To estimate ϕ, the rate constants k are measured at or extrapolated to the same conditions by determining lnk vs. the amount of denaturing agent. The folding nucleus of FGF-1 was determined by ϕ-value analysis in Longo, et al., *Protein Science*, 21, 1911-1920, which is hereby incorporated by reference.

Another experimental technique for identifying the folding nucleus of the reference protein is to take regions of the reference protein's sequence and make an artificial protein by expanding such sequences by the symmetry of the target architecture, expressing them as recombinant proteins, and determining which sequences can efficiently fold.

From the folding nucleus, a folding nucleus peptide sequence is selected. The folding nucleus peptide sequence is a peptide sequence determined to be in the folding nucleus and which has substantial homology with the peptide sequence determined as described above. The folding nucleus peptide sequence is then used as a basis for synthesizing the synthetic protein.

Through a substantially symmetric expansion of the folding nucleus peptide sequence, the synthetic protein having a tertiary structure emulating the reference protein tertiary structure is produced. The synthetic protein, therefore, is formed from the folding nucleus peptide sequence, which is repeated throughout the synthetic protein.

The primary structure of the synthetic protein and the symmetry of its tertiary structure are inter-related. The number of symmetry operations that can be performed on the reference foldable protein is equal to a number of tandem repeats of the determined folding nucleus peptide sequence in the peptide sequence of the synthetic foldable protein. A "symmetry operation" is a movement of a protein that, after the movement has been carried out, each point on the protein is substantially coincident with an equivalent point of the protein in its original orientation. For folded proteins, the symmetry operation will typically be a rotation, but it may also be a translation, as would be the case with linear repeat proteins. β-trefoil proteins, for example, have three-fold rotational symmetry and the synthetic protein includes three tandem repeats of the folding peptide sequence.

Even though the synthetic protein has a different primary structure than the reference protein, the synthetic protein still emulates the symmetry of the reference protein. The primary structure of the synthetic protein may be symmetric, meaning the repeated folding peptide segment makes up the primary structure. The tertiary structure of the synthetic protein may also be symmetric. In some examples, the synthetic protein may have exact sequence symmetry, meaning the primary structure and the tertiary structure are symmetric.

The synthetic protein may be synthesized using conventional protein synthesis techniques such as liquid-phase synthesis, solid-phase synthesis, and/or by recombinant expression and purification. Although, an example of an expression and purification process is described in more detail below, this is not intended to limit the scope of possible synthesis techniques.

The expression and purification technique involves obtaining artificial genes with the desired nucleic acid sequence for expressing the synthetic protein with the desired polypeptide sequence. Expression of the synthetic protein may be performed by bacteria cells. The cells are subsequently lysed and the synthetic protein is purified from the lysed cells.

The method provides a strategy to design an efficient folding and stable protein. The fundamental architecture of the resulting design belongs to the broad category of symmetric protein architectures, which involve many common protein folds. A basic de novo protein design principle is to first design a robustly folding, but functionally benign, "scaffold"- and to then introduce subsequent design changes or mutations to introduce a specific desired or novel functionality. In this regard, there is a parallel to synthetic organic chemistry and the initial synthesis of a useful molecular scaffold followed by derivatization to create new agents having the basic scaffold structure.

In the case of proteins, certain fundamental and symmetric protein architectures have specific useful and common functionalities in nature. For example, the basic beta-trefoil architecture is common in proteins that function as protease inhibitors, cytokines, lectins, and muscle-binding proteins. The TIM-barrel architectures are useful for making aldo-keto reductase and other types of enzymes. The beta-propeller architecture is common in lectins and other enzymes as well.

Aside from making useful synthetic proteins, the synthetic protein itself may be used to design other synthetic proteins with useful functions. For example, to design a new protease inhibitors, one would first design a folding and thermostable beta-trefoil scaffold and then subsequently mutate specific positions to introduce the desired inhibitor function.

Example: Preparation and Characterization of an Synthetic Protein Emulating the Structure of FGF-1

This section provides a specific example of an embodiment of the method and composition. This example is provided to illuminate certain details of the exemplary embodiments. The scope of the possible embodiments is not limited to what this example teaches.

FGF-1, which corresponds to SEQ ID NO: 1 was selected as the reference protein. FGF-1 has a β-trefoil structure. Its folding nucleus was identified in Longo, et al., *Protein Science,* 21, 1911-1920 (2012) by ϕ-value analysis. Longo, et al. is incorporated by reference in its entirety.

The synthetic protein, referred to in this example as "Phifoil," was prepared and characterized as described below. The amino acid sequence of Phifoil corresponds to SEQ ID NO: 2.

FIG. 1 shows a secondary structure schematic for illustrating how the protein synthesis method was applied using FGF-1 as the reference protein. FIG. 1A depicts the secondary structure schematic of FGF-1 with the repeating trefoil-fold structural subdomains indicated by the boxes. The arrows indicate β-strands, and the cylinders indicate helices. The solid bars indicate loops and surface turns. The amino acid numbering scheme of the 140 amino acid form of FGF-1 is used throughout.

FIG. 1C depicts the location of the folding nucleus (solid) of FGF-1 as determined from experimental ϕ-value analysis. FIG. 1D illustrates how Phifoil was designed using a folding peptide segment from the folding nucleus of FGF-1 expanded by the three-fold symmetry of the β-trefoil target architecture. It also illustrates the associated secondary structure elements derived from FGF-1.

The primary structure of the folding peptide sequence from the FGF-1 folding nucleus was internally propagated using a three-fold symmetry operator to all equivalent positions throughout the entire β-trefoil tertiary structure to generate a symmetric protein scaffold in a single design step.

Phifoil is an efficiently folding polypeptide that correctly adopts the β-trefoil target architecture. Further-more, Phifoil is more thermostable and significantly less aggregation prone during thermal unfolding than FGF-1. Phifoil, unlike FGF-1, is well-described by cooperative two-state models of protein folding. Notably, the exact three-fold symmetry of the primary structure within Phifoil provides the potential for redundant (i.e., two intact and one interrupted, or three circularly permuted) folding nuclei-any one of which may be sufficient for foldability.

FIG. 2 shows a comparison between the primary structures of FGF-1 and Phifoil. The primary structures are arranged according to the three repeating trefoil-fold structural subdomains. The numbering scheme is based on FGF-1 with the relative gaps or insertions indicated. The contiguous amino acid positions 23-64, which are shaded in the darker color, identify the folding nucleus of FGF-1 that was expanded by the three-fold symmetry of the β-trefoil architecture to construct Phifoil (FIG. 1C). Additional lighter shaded positions identify identical amino acids between FGF-1 and Phifoil in the remaining regions of the protein-showing that the primary structure of the folding nucleus exhibits minimal identity with the other symmetry-related positions in FGF-1.

Referring to FIG. 3, ϕ-value analysis on FGF-1 revealed that the folding nucleus of FGF-1 spans turn #2 to #5. The specific peptide sequence segment of the subsequent folding nucleus design element was chosen such that each of the pertinent turns identified by ϕ-value analysis would be incorporated in the resulting folding peptide segment. Accordingly several amino acids before turn #2 and after turn #5 were included.

Referring back to FIG. 2, the peptide segment used to create Phifoil (dark shading) spanned residues 23-64 or, equivalently, residues 24-65. This 42-residue region is one-third of the overall β-trefoil protein structure. It is somewhat smaller, however, than the entire folding nucleus region identified by φ-value analysis.

The symmetric expansion of this sequence to structurally equivalent positions meant that the missing parts of the experimentally determined folding nucleus were regenerated by structurally equivalent residues from positions residing within the folding nucleus. Alternative definitions involving minor variations in the precise start point may serve equally well as efficient folding nuclei.

The Phifoil structure was generated by symmetric expansion of the region 23-64 (24-65) folding nucleus but retaining the wild-type β-trefoil N- and C-terminus definitions. Thus, the Phifoil polypeptide contains two intact folding nuclei from FGF-1 as well as one interrupted folding nucleus, partial regions of which are located at the N- and C-termini. Alternatively, if circular permutation does not destroy the properties of the folding nucleus, then Phifoil contains three intact, but circularly permuted, FGF-1 folding nuclei.

Synthesis of Phifoil.

Artificial genes were ordered from Integrated DNA technologies (Coralville, Iowa) and sequenced prior to protein expression. The Phifoil sequence included an amino-terminal 6×His-tag to permit efficient purification. The *E. coli* BL21(DE3) (Novagen, Darmstadt, Germany) expression system was used, as previously described in Blaber et al., *Biophys J.*, 77, 470-477 (1999), which is incorporated by reference in its entirety.

The cells were lysed by passing them through a French pressure cell and were clarified by centrifugation (7,500×g for 15 min). Purification by nickel affinity chromatography followed by gel filtration on a 26/60 Superdex 75 preparative column and resolved using an AKTA FPLC system (GE Healthcare, Little Chalfont, United Kingdom), resulted in sample purities greater than 98% (as assessed by densitometry of Coomassie blue stained 15% sodium dodecyl sulfate-polyacrylamide gels). Purified protein yield of Phifoil was about 60 mg per liter of culture. The extinction coefficient of Phifoil was determined to be 0.474 mL/mg/cm.

The sequence of Phifoil was extracted directly, with no mutational change, from the folding nucleus peptide segment of wild-type FGF-1 based on the previously reported φ-value analysis for FGF-1. As a consequence of this, all three structural subdomains, the trefoil-folds, of Phifoil exhibited 100% sequence identity. Conversely, there is only one symmetry-related position in FGF-1 in which all three subdomains share the same amino acid, which is a Gly residue at positions 29, 71, 115. The size of the amino acid alphabet in Phifoil is reduced since only 15 of the 20 amino acid types present in FGF-1 were contained within the Phifoil sequence (Asn, Cys, Met, Phe, and Trp are excluded). Thus, Phifoil had both exact primary structure symmetry and a reduced amino acid alphabet.

The regions comprising residue positions 11-52, 53-93, and 94-140 define the three repeating "trefoil-fold" subdomains in FGF-1 (FIG. 2). Three different β-trefoil constructs were prepared by symmetric expansion of these domains (i.e., utilizing a structure-based motif, not a folding nucleus-based motif). Expression and purification of these three β-trefoil proteins (i.e., symmetric expansion of regions of FGF-1 not containing an intact folding nucleus) was attempted but failed in each case.

The constructs derived from the first β-trefoil subdomain and the third β-trefoil subdomain precipitated upon cell lysis. The construct derived from the second β-trefoil subdomain failed to express.

X-Ray Crystallography of Phifoil.

For crystallization studies, Phifoil samples were dialyzed into a phosphate buffer containing 50 mM $NaP_i$, 100 mM NaCl, 10 mM $(NH_4)_2SO_4$, having a pH of 7.5. Purified Phifoil in phosphate buffer was concentrated to about 12 mg/mL and crystal conditions were screened using the hanging-drop vapor diffusion method at 25° C. Diffraction quality crystals grew in about 1 month from vapor diffusion against 800 mM $(NH_4)_2SO_4$, 100 mM citric acid at pH=4.

A crystal was mounted using a Hampton Research nylon cryo-loop and cooled in a stream of gaseous nitrogen to 100 K. Diffraction data were collected using an in-house Rigaku RU-H3R rotating anode X-ray source (Rigaku, Tokyo, Japan) equipped with Osmic confocal mirrors (Osmic Inc., Troy, Mich.) and a MarCCD165 (Rayonix, Evanston, Ill.) detector. The data were indexed, integrated, and scaled using the HKL2000 software package. Molecular replacement and model building utilized the PHENIX software package, with 5% of the data in the reflection files set aside for $R_{free}$ calculations. PDB accession 3O49 was used as the search model in molecular replacement.

FIG. 4 provides the X-ray structure refinement data of Phifoil. The structure was solved to 2.15 Å. Phifoil adopts an idealized (i.e., purely-symmetric) β-trefoil architecture with the major structural differences compared to FGF-1 localized to regions of relative insertions/deletions ($RMSD_{C\alpha}$ for conserved regions=1.0 Å). Structural analysis of the β-trefoil fold highlights 15 key positions that form a solvent-excluded, central hydrophobic packing group. In Phifoil, these positions are excluded from solvent (as determined by a 1.2 Å radius probe), whereas in FGF-1, this set demonstrates a partial solvent accessible surface area of 15.9 Å$^2$, the principle contributors being Leu14, Val109, and Cys117.

Figure 10A:
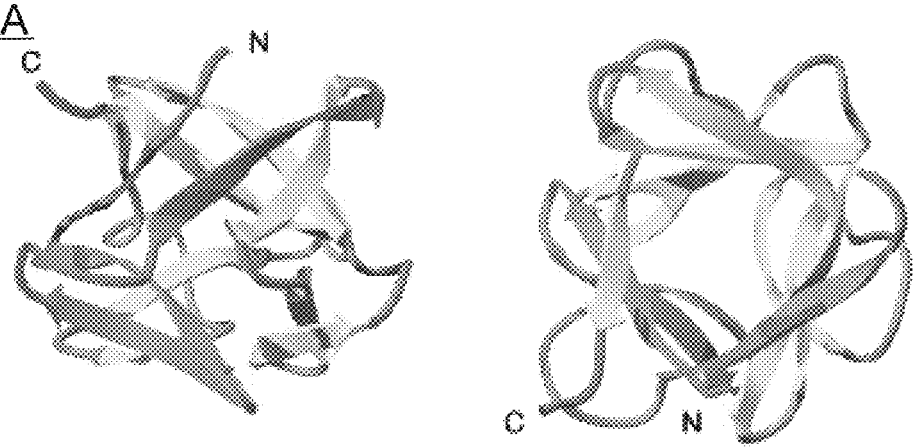
FIG. 10A is a ribbon diagram of FGF-1 (side view on left; top view parallel to the threefold axis of rotational symmetry on right). The blue region identifies the three-fold repeating trefoil-fold structural subdomain. (PDB accession 2AFG)
Figure 10B:
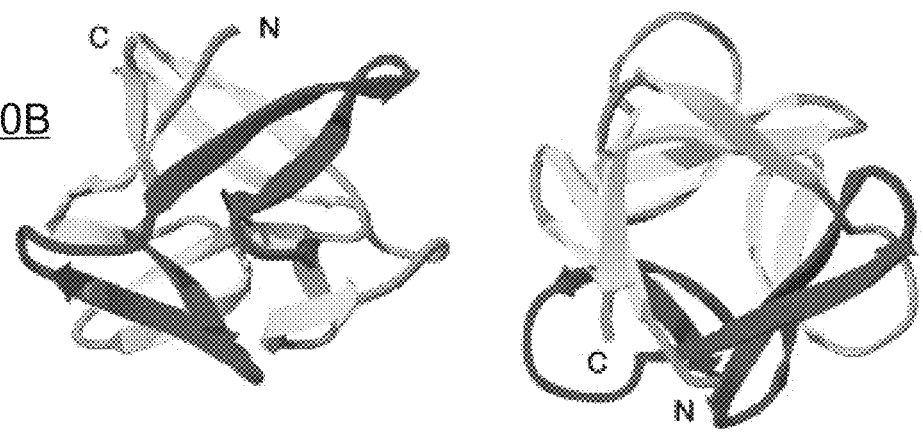
FIG. 10B is a ribbon diagram of Phifoil in substantially the same orientations as FIG. 10A. The red region identifies residue positions 23-64, the folding nucleus extracted from FGF-1 and expanded by the intrinsic three-fold symmetry to generate the substantially purely symmetric Phifoil primary structure.

FIG. 5 provides a comparison between the core packing parameters for FGF-1 vs. Phifoil. FIGS. 10A and 10B provide a comparison of the three-dimensional ribbon diagram structure between FGF-1 and Phifoil.

Isothermal Equilibrium Denaturation Studies.

Phifoil was placed in an ADA buffer containing 20 mM N-(2-Acetamido)iminodiacetic acid, 100 mM NaCl having a pH of 6.6.

10 μM samples of Phifoil in ADA Buffer were incubated for about 20 h at 25° C. in the presence of 0.0-2.6 M GuHCl (i.e., 2×$C_m$) in 0.1 M increments. The folding of Phifoil was monitored by fluorescence on a Cary Eclipse fluorospectrophotometer equipped with a Peltier temperature control unit (Agilent, Santa Clara, Calif.). Samples were loaded into a 1.0 cm path length quartz cuvette and were incubated for 4 min prior to collecting spectra. Tyr fluorescence was excited at 277 nm, emission was monitored from 284-410 nm, and slit-widths were set to 5 nm.

Each sample was scanned in triplicate and the resulting spectra were averaged, buffer subtracted, and integrated to generate an unfolding curve. The resulting unfolding curve was fit to a 6-parameter, two-state model of protein unfolding using the non-linear, least squares fitting program, DataFit (Oakdale Engineering, Oakdale, Pa.). Reported errors are the standard deviation of three independent experiments.

Results from the isothermal equilibrium denaturation studies are provided in FIGS. 6 and 9A.

Chemical denaturation by guanidinium hydrochloride (GuHCl) of both FGF-1 and Phifoil was well-described by a two-state unfolding model (FIG. 9A). The unfolding transition of both proteins is cooperative, but Phifoil exhibits a ~10% reduction in m-value compared to FGF-1, presumably reflecting its smaller size ($L_{Phifoil}$=126 residues; $L_{FGF-1}$=140 residues). The predicted m-value for Phifoil based on the number of ordered residues in the crystal structure is only slightly lower than the experimentally determined value ($m_{pred}$=16.1 kJ/mol/M, $m_{obs}$=17.5 kJ/mol/M), suggesting that the Phifoil unfolding reaction spans an ordered native state and an unstructured unfolded state. Both proteins possess similar stability at 25 degrees C. in the absence of denaturant, with $\Delta G_{unf}$=21.9±0.3 kJ/mol and 20.7±0.3 kJ/mol for FGF-1 and Phifoil, respectively.

Differential Scanning Calorimetry Studies.

Phifoil was placed in an ADA buffer containing 20 mM N-(2-Acetamido)iminodiacetic acid, 100 mM NaCl having a pH of 6.6. Differential scanning calorimetry (DSC) was performed on samples of 40 µM Phifoil in ADA buffer using a VP-DSC microcalorimeter (GE Healthcare, Little Chalfont, United Kingdom). Samples were scanned from 10-95° C. under 2.3 bar, with a pre-scan equilibration time of 10 min and a scan rate of 0.25° C./min. Prior to protein loading, buffer-buffer scans were collected until thermal history was established. Buffer-subtracted, concentration-normalized endotherms were analyzed using the DSCFit software package and standard deviations result from three consecutive protein loads.

Results from the DSC studies are provided in FIGS. 7 and 9B.

The thermal unfolding of Phifoil is different than FGF-1 (FIG. 9B) as assessed by DSC. Unfolding of FGF-1 is non-cooperative and characterized by significant aggregation near the unfolding transition, which is presented as an exothermic signal subsequent to unfolding and with visible precipitation in recovered samples. As such, thermodynamic parameters describing the thermal denaturation of FGF-1 without denaturant cannot be directly determined.

In contrast, Phifoil denaturation was well-described by a two-state model of protein unfolding, with $\Delta H_{van't\,Hoff}/\Delta H_{cal}$ equal to unity. Further, Phifoil unfolding is associated with a significant positive $\Delta C_p$, as expected for exposure of hydrophobic residues to solvent upon denaturation.

Empirical Phase Diagrams.

For an empirical phase diagram determination, Phifoil samples were placed in a 20 mM citrate-phosphate buffer with an ionic strength=0.15 adjusted with NaCl and having a pH of 3-8. Temperature vs. pH empirical phase diagrams (EPDs) were generated using three probes of protein structure: circular dichroism (CD), static light scattering (SLS), and extrinsic fluorescence. Temperatures ranged from 10-87.5° C. pH values ranged from 3-8. Each probe at each pH was measured in triplicate and averaged to yield the final data for EPD determination. Three-index EPDs were constructed as previously described using the MiddaughSuite software package.

Circular dichroism was performed using a Chirascan-plus CD spectrometer (Applied Photophysics Ltd, Leatherhead, UK) equipped with a 4-cuvette position Peltier temperature controller (Quantum Northwest, Liberty Lake, Wash.). Far-LTV CD spectra were collected in the range of 260-200 nm in 1 nm steps and a 0.5 s sampling time at each wavelength. Quartz cuvettes (0.1 cm path length) sealed with teflon stoppers (Starna Cells Inc., Atascadero, Calif.) were used. The CD signal at 230 nm was monitored as a function of temperature from 10.0-87.5° C. at 2.5° C. intervals. The heating rate was 1° C./min, and the equilibration time at each temperature was 1 min. The ellipticity of the buffer was subtracted from all measurements. All data were subjected to a 3-point Savitzky-Golay smoothing filter using the Chirascan software (Applied Photophysics Ltd, Leatherhead, UK).

Light scattering was measured by exciting tyrosine at 280 nm and measuring the scattered light at the excitation wavelength. Experiments were performed using a PTI QM-40 spectrofluorometer (Photon Technology International, Birmingham, N.J.) equipped with a 4-cell position Peltier temperature controller (Quantum Northwest, Liberty Lake, Wash.). Samples were heated from 10.0-87.5° C. in 2.5° C. increments with a 2 min equilibration time at each temperature. Excitation and emission slits were set at 2 and 0.25 nm, respectively. The light scattering intensity of the buffer was subtracted from all measurements prior to data analysis.

Accessibility of hydrophobic moieties as a function of temperature was assessed using 8-anilino-l-naphthalenesulfonate ((ANS), Sigma-Aldrich, St. Louis, Mo.). ANS (solubilized in DMSO) was added to Phifoil at a 15:1 molar ratio and incubated in the dark for at least 5 min at 10° C. Samples were measured using an excitation wavelength of 372 nm and the emission spectrum was monitored from 400 to 600 nm as a function of temperature (10-87.5° C.). The excitation and emission slits were both set at 3 nm. Step size and integration time were 1 nm and 0.5 s, respectively. The spectra were collected at 2.5° C. intervals with a 2 min equilibration time at each temperature. One cm quartz cuvettes were used in all experiments. Fluorescence intensity at 480 nm was plotted as a function of temperature and emission of the buffer containing ANS was subtracted from all measurements.

Figure 8B:
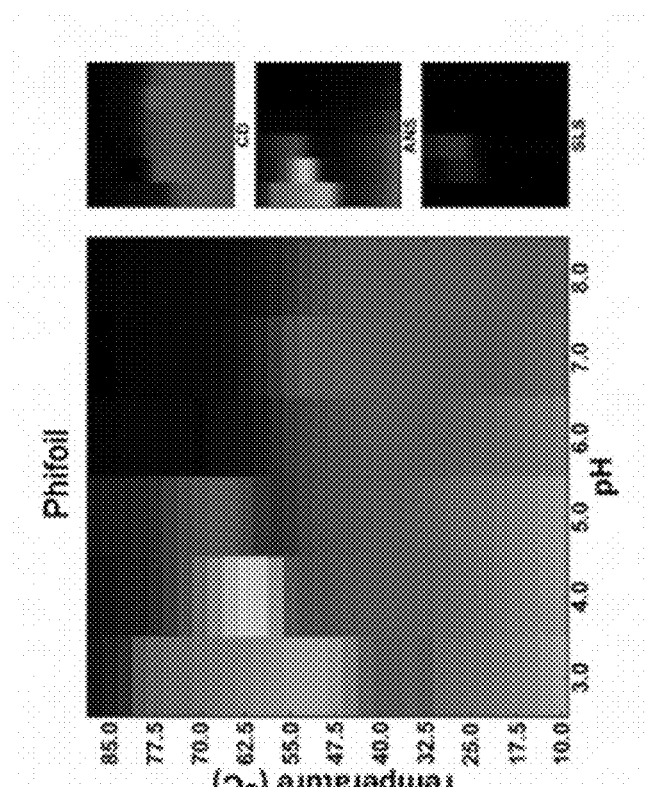
FIG. 8B (left) is a composite pH vs. temperature empirical phase diagram of Phifoil combining data from circular dichroism (CD), ANS binding, and static light scattering (SLS) experiments (right). The red color indicates native-like secondary structure. The green color indicates partially folded or molten-globule-like states. The blue color indicates protein aggregation.
Figure 8A:
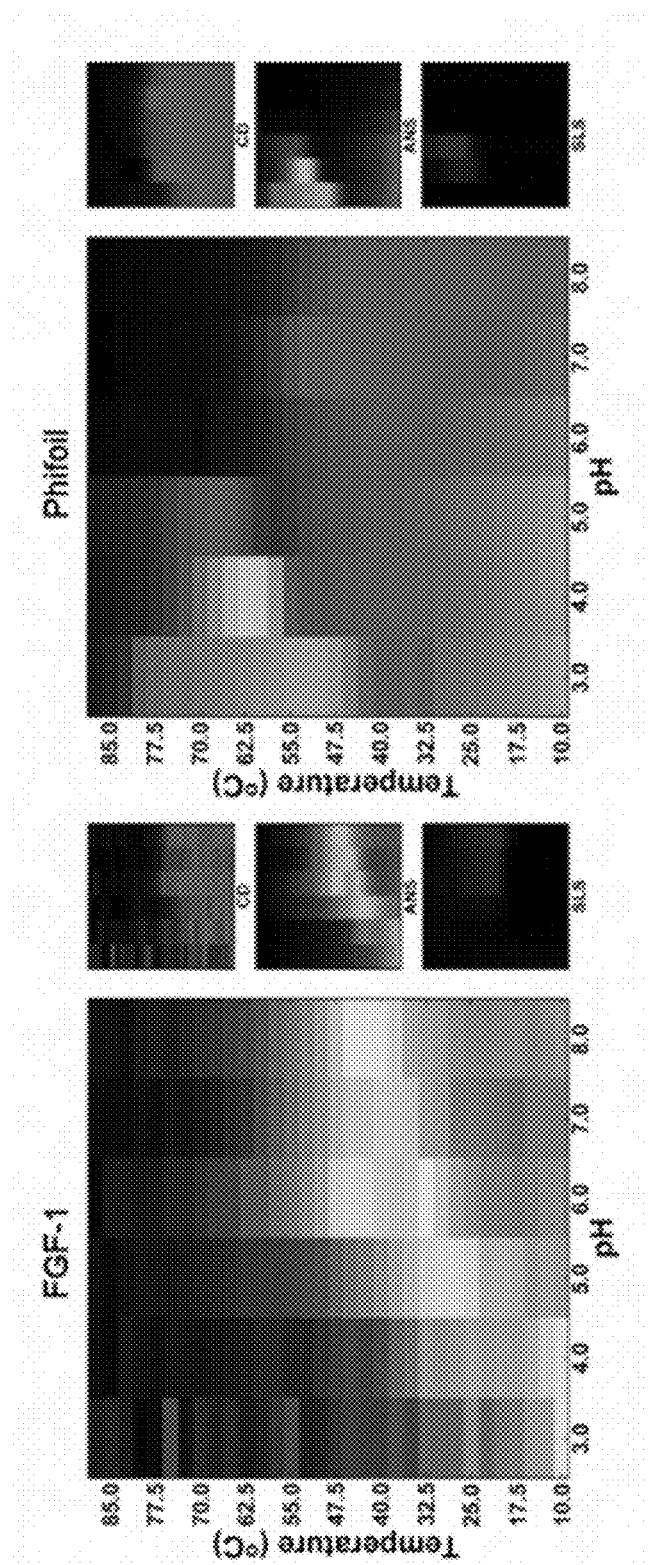
FIG. 8A (left) is a composite pH vs. temperature empirical phase diagram of FGF-1 combining data from circular dichroism (CD), ANS binding, and static light scattering (SLS) experiments (right). The red color indicates native-like secondary structure. The green color indicates partially folded or molten-globule-like states. The blue color indicates protein aggregation.

Results from the empirical phase diagram studies are provided in FIG. 8. The diagrams were constructed using three structural probes: circular dichroism (CD), in which the red color indicates native-like secondary structure; ANS binding, in which green color indicates partially folded or molten-globule-like states; and static light scattering (SLS), in which blue color indicates protein aggregation. Individual contributions from each probe are shown on the right; with the large images showing the additive overlay of all probe data.

This disclosure describes preferred embodiments, but not all possible embodiments of the compositions and methods. Where a particular feature is disclosed in the context of a particular composition or method, that feature can also be used, to the extent possible, in combination with and/or in the context of other embodiments of the compositions and methods. The compositions and methods may, be embodied in many different forms and should not be construed as limited to only the embodiments described here.

That which is claimed is:

1. A method of making a foldable protein, the method comprising:

determining a folding nucleus peptide sequence associated with folding a reference foldable protein, the reference foldable protein having a tertiary structure; and synthesizing a synthetic foldable protein having a tertiary structure emulating the tertiary structure of the reference foldable protein by including the determined folding nucleus peptide sequence and at least one repeat thereof in the peptide sequence of the synthetic foldable protein by expressing the synthetic foldable protein in one expression step;

wherein the synthetic foldable protein comprises SEQ ID NO: 2.

2. The method of claim 1, wherein the step of determining the folding nucleus peptide sequence of the reference foldable protein comprises identifying the folding nucleus of the reference foldable protein by performing φ-value analysis on the reference foldable protein.

3. The method of claim 1, wherein the number of symmetry operations that can be performed on the reference foldable protein is equal to a number of tandem repeats of the determined folding nucleus peptide sequence in the peptide sequence of the synthetic foldable protein.

4. The method of claim 1, wherein the tertiary structure of the synthetic foldable protein has substantially the same symmetry as the tertiary structure of the reference foldable protein.

5. The method of claim 1, wherein the reference foldable protein is native human FGF-1.

6. The method of claim 1, wherein the folding nucleus peptide sequence comprises SEQ ID NO: 3.

7. The method of claim 1, wherein the synthetic foldable protein has a β-trefoil structure, TIM-barrel, or beta-propeller structure.

8. A method of making a foldable protein, the method comprising:

(a) determining a folding nucleus peptide sequence associated with folding a reference foldable protein, the reference foldable protein having a tertiary structure; and (b) forming a synthetic foldable protein through symmetric expansion of the folding nucleus peptide sequence determined in step (a) by:

(i) contacting a cell with a gene encoding for the synthetic foldable protein; and (ii) allowing the cell to express the synthetic foldable protein;

wherein a peptide sequence of the synthetic foldable protein expressed in step (b) includes a plurality of tandem repeats of the folding nucleus peptide sequence and emulates the tertiary structure of the reference foldable protein when folded;

wherein the synthetic foldable protein comprises SEQ ID NO: 2.

9. The method of claim 8, wherein the step of determining the folding nucleus peptide sequence of the reference foldable protein comprises identifying the folding nucleus of the reference foldable protein by performing φ-value analysis on the reference foldable protein.

10. The method of claim 8, wherein the number of symmetry operations that can be performed on the reference foldable protein is equal to a number of tandem repeats of the determined folding nucleus peptide sequence in the peptide sequence of the synthetic foldable protein.

11. The method of claim 8, wherein the tertiary structure of the synthetic foldable protein has substantially the same symmetry as the tertiary structure of the reference foldable protein.

12. The method of claim 8, wherein the reference foldable protein is native human FGF-1.

13. The method of claim 8, wherein the folding nucleus peptide sequence comprises SEQ ID NO: 3.

14. The method of claim 8, wherein the synthetic foldable protein has a β-trefoil structure, TIM-barrel, or beta-propeller structure.

\* \* \* \* \*